US012758801B2

(12) United States Patent
Ueyama et al.

(10) Patent No.: US 12,758,801 B2
(45) Date of Patent: Oct. 13, 2026

(54) ULTRASONIC TRANSDUCER INSPECTION DEVICE AND INSPECTION METHOD

(71) Applicant: SONIRE THERAPEUTICS INC., Tokyo (JP)

(72) Inventors: Tsuyoshi Ueyama, Tokyo (JP); Jun Okamoto, Tokyo (JP)

(73) Assignee: SONIRE THERAPEUTICS INC., Tokyo (JP)

( * ) Notice: Subject to any disclaimer, the term of this patent is extended or adjusted under 35 U.S.C. 154(b) by 390 days.

(21) Appl. No.: 18/694,599

(22) PCT Filed: Nov. 19, 2021

(86) PCT No.: PCT/JP2021/042586
§ 371 (c)(1),
(2) Date: Mar. 22, 2024

(87) PCT Pub. No.: WO2023/047605
PCT Pub. Date: Mar. 30, 2023

(65) Prior Publication Data

US 2024/0390705 A1 Nov. 28, 2024

(30) Foreign Application Priority Data

Sep. 22, 2021 (JP) ................................ 2021-154673

(51) Int. Cl.
*A61N 7/02* (2006.01)
*A61N 7/00* (2006.01)
*G01S 7/52* (2006.01)

(52) U.S. Cl.
CPC ............ *A61N 7/02* (2013.01); *G01S 7/52057* (2013.01); *A61N 2007/0078* (2013.01)

(58) Field of Classification Search
CPC .............. A61N 7/02; A61N 2007/0078; G01S 7/52057; A61B 8/00; A61B 8/14
See application file for complete search history.

(56) References Cited

U.S. PATENT DOCUMENTS 5,553,618 A 9/1996 Suzuki et al.
5,722,411 A 3/1998 Suzuki et al.
(Continued)

FOREIGN PATENT DOCUMENTS

JP H07-47079 A 2/1995
JP H08-071069 A 3/1996
(Continued)

OTHER PUBLICATIONS

Office Action in parent Japanese application No. 2021-154673, Jan. 11, 2022, with machine translation (10 pages).
(Continued)

*Primary Examiner* — Daryl C Pope
(74) *Attorney, Agent, or Firm* — ICE MILLER LLP; Justin D. Swindells

(57) ABSTRACT

Method of facilitating inspection of an ultrasonic transducer used in high-intensity focused ultrasound therapy. Selection and observation processing is performed by: (i) processing for selecting one pair of divided surfaces from multiple pairs of divided surfaces obtained by dividing a bowl-shaped surface at multiple cutting planes that include the central axis of the bowl-shaped surface; (ii) processing for causing ultrasonic transducers disposed on the one pair of divided surfaces selected from the multiple pairs of divided surfaces to transmit ultrasonic waves; (iii) processing for setting an ultrasonic probe to a state in which an ultrasonic beam is scanned on an observation surface that passes through the pair of divided surfaces selected from the multiple pairs of divided surfaces; and (iv) processing for acquiring ultrasound date regarding the observation surface on which the ultrasonic beam was scanned.

9 Claims, 5 Drawing Sheets

(56) References Cited

U.S. PATENT DOCUMENTS

| | | | | |
|---|---|---|---|---|
| 12,635,974 | B2 * | 5/2026 | Dayton ................ | A61B 8/0891 |
| 2008/0051656 | A1 | 2/2008 | Vaezy et al. | |
| 2008/0167555 | A1 | 7/2008 | Qian et al. | |
| 2025/0134488 | A1 * | 5/2025 | Kaouk ..................... | A61B 8/12 |

FOREIGN PATENT DOCUMENTS

| | | | |
|---|---|---|---|
| JP | 2014-094172 | A | 5/2014 |
| WO | 2015/186651 | A1 | 12/2015 |

OTHER PUBLICATIONS

English translation of International Search Report in parent application No. PCT/JP2021/042586, Feb. 15, 2022 (2 pages).

* cited by examiner

ULTRASONIC TRANSDUCER INSPECTION DEVICE AND INSPECTION METHOD

CROSS-REFERENCE TO RELATED APPLICATIONS

This application is a National Stage of International Application No. PCT/JP2021/042586, filed Nov. 19, 2021, which claims priority to Japan Patent Application No. 2021-154673 filed Sep. 22, 2021, the disclosures of which are incorporated herein by reference in their entirety.

TECHNICAL FIELD

The present invention relates to an inspection device for an ultrasonic transducer and an inspection method for the same, and, in particular, relates to a technique for inspecting a plurality of ultrasonic transducers arranged along a bowl-shaped surface.

BACKGROUND

Medical treatment devices employing a high intensity focused ultrasound therapeutic method have been widely used. Such a medical treatment device is referred to as a HIFU (High Intensity Focused Ultrasound) radiation device or a HIFU irradiation system and is configured to irradiate a treatment site with ultrasound waves in order to necrose tissue.

In general, the HIFU irradiation device is equipped with a plurality of ultrasonic transducers arranged along a bowl-shaped surface. The plurality of ultrasonic transducers are arranged in such a manner that ultrasound waves respectively emitted from the plurality of ultrasonic transducers are irradiated on a single point so as to form a focal point. In a medical treatment, a position of the focal point is matched with a treatment site to irradiate the treatment site with ultrasound waves. An irradiation position is confirmed using an ultrasound diagnostic apparatus which represents the focal point on an ultrasound image.

Patent Document 1 listed below describes an ultrasound treatment apparatus in which the position of a focal point is observed using an ultrasound diagnostic apparatus which displays a B mode image (tomographic image). In this apparatus, ultrasound waves are emitted from therapeutic ultrasonic transducers at a weaker level at which no effect is exerted on tissue, and a tomographic image is displayed through transmission and reception of ultrasound waves by an ultrasound imaging probe. Because acoustic characteristics of tissue in an examination subject are varied due to a change in temperature of the tissue, the position of the focal point is indicated by the degree of brightness on the tomographic image.

Below-listed Patent Document 2 describes a technique for evaluating a displacement of an irradiation position and a displacement of an irradiation path before performing a treatment according to a high intensity focused ultrasound therapeutic method.

CITATION LIST

Patent Literature

PATENT DOCUMENT 1: JP H08-71069 A
PATENT DOCUMENT 2: JP H07-47079 A

SUMMARY

Technical Problem

In HIFU irradiation devices, properties of an ultrasonic transducer may be changed due to an impact exerted from the outside, variations by aging, and other factors. Such a change may cause the focal point to be deviated from an ideal position or reduce the intensity of a therapeutic ultrasound wave at the focal point. With this in view, it has been desired to establish a technique for performing an inspection of the ultrasonic transducer in a simple manner.

It is an object of the present invention to facilitate an inspection of an ultrasonic transducer used for a high intensity focused ultrasound therapeutic method.

Solution to Problem

The present invention relates to an ultrasonic transducer inspection apparatus characterized by including a transducer controlling device configured to control a plurality of ultrasonic transducers arranged along a bowl-shaped surface, a probe driving device configured to rotate an ultrasound probe positioned at the center axis of the bowl-shaped surface around the center axis, a data acquiring device configured to acquire ultrasound data using the ultrasound probe, and a controller configured to control the transducer controlling device, the probe driving device, and the data acquiring device. In the ultrasonic transducer inspection apparatus, the controller controls the transducer controlling device to transmit an ultrasound wave from the ultrasonic transducer positioned at a pair of segmented surfaces opposed to each other across the center axis, the pair of segmented surfaces being contained in a plurality of segmented surfaces obtained by segmenting the bowl-shaped surface at a plurality of cutting planes containing the center axis, controls the probe driving device to set the ultrasound probe in a state of scanning an ultrasound beam in an observation plane passing through the pair of segmented surfaces, and controls the data acquiring device to acquire the ultrasound data on the observation plane where the ultrasound beam is scanned.

Preferably, the controller is configured to find, based on the ultrasound data, an ultrasound intensity at a treatment datum point defined for the plurality of ultrasonic transducers, and display on a display device information associated with the ultrasound intensity.

Preferably, the controller is configured to perform a selection and observation process, the selection and observation process including selecting the pair of segmented surfaces from a plurality of pairs of segmented surfaces opposed to each other across the center axis, controlling the transducer controlling device to transmit an ultrasound wave from the ultrasonic transducer positioned at the pair of segmented surfaces selected from the plurality of pairs of segmented surfaces, controlling the probe driving device to set the ultrasound probe in a state of scanning an ultrasound beam in an observation plane passing through the pair of segmented surfaces selected from the plurality of pairs of segmented surfaces, and controlling the data acquiring device to acquire the ultrasound data on the observation plane where the ultrasound beam is scanned, and the selection and observation process is performed on each of the plurality of pairs of segmented surfaces.

Preferably, the controller is configured to perform, on each of the plurality of pairs of segmented surfaces, a process to find, based on the ultrasound data, an ultrasound intensity at a treatment datum point defined for the plurality of ultrasonic transducers, and display, on a display device, information associated with the ultrasound intensity found for the each of the plurality of pairs of segmented surfaces.

Preferably, the controller is configured to perform, on each of the plurality of pairs of segmented surfaces, a process to find, based on the ultrasound data, an ultrasound intensity at a treatment datum point defined for the plurality of ultrasonic transducers, and determine, based on the ultrasound intensity found for the each of the plurality of pairs of segmented surfaces, states of the ultrasonic transducers which are respectively associated with the plurality of pairs of segmented surfaces.

Preferably, the controller is configured to perform, on each of the plurality of pairs of segmented surfaces, a process to find, based on the ultrasound data, an ultrasound intensity at a treatment datum point defined for the plurality of ultrasonic transducers, and determine, based on a comparison between a reference value and the ultrasound intensity found for each of the plurality of pairs of segmented surfaces, states of the ultrasonic transducers which are respectively associated with the plurality of pairs of segmented surfaces.

Further, the present invention relates to an inspection method for inspecting a plurality of ultrasonic transducers arranged along a bowl-shaped surface, the inspection method characterized by including performing a selection and observation process composed of selecting a pair of segmented surfaces from a plurality of pairs of segmented surfaces obtained by segmenting the bowl-shaped surface at a plurality of cutting planes containing the center axis of the bowl-shaped surface, the plurality of pairs of segmented surfaces being opposed to each other across the center axis, transmitting an ultrasound wave from the ultrasonic transducer positioned at the selected pair of segmented surfaces, setting an ultrasound probe in a state of scanning an ultrasound beam in an observation plane passing through the selected pair of segmented surfaces, and acquiring ultrasound data on the observation plane where the ultrasound beam is scanned, the selection and observation process being performed on each of the plurality of ultrasonic transducers, and further including determining, based on the ultrasound data acquired for the each of the plurality of pairs of segmented surfaces, states of the ultrasonic transducers which are respectively associated with the plurality of pairs of segmented surfaces.

Preferably, determining states of the ultrasonic transducers which are respectively associated with the plurality of pairs of segmented surfaces includes performing, on the each of the plurality of pairs of segmented surfaces, a process to find, based on the ultrasound data, an ultrasound intensity at a treatment datum point defined for the plurality of ultrasonic transducers, and determining, based on the ultrasound intensity found for the each of the plurality of pairs of segmented surfaces, the states of the ultrasonic transducers which are respectively associated with the plurality of ultrasonic transducers.

Advantageous Effects of Invention

According to the present invention, the ultrasonic transducer used for a high intensity focused ultrasound therapeutic method can be easily inspected.

DESCRIPTION OF EMBODIMENTS

Figure 1:
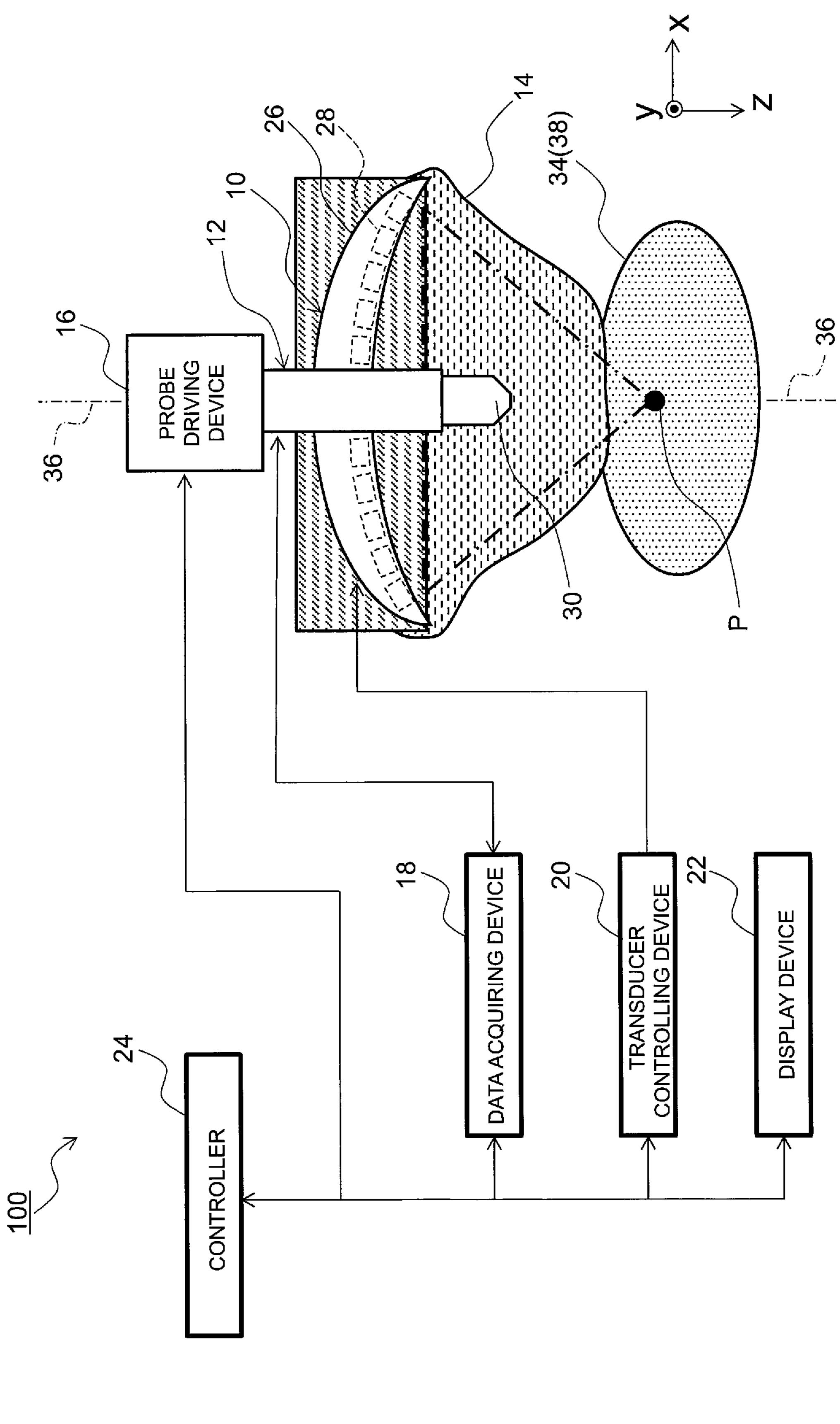
FIG. 1 is a diagram showing a configuration of a HIFU irradiation system.

An embodiment of this invention will be explained with reference to the drawings. Identical components shown in a plurality of diagrams are identified by identical reference signs, and repeated description related to those components will be simplified. The terms above, below, left, and right as used herein represent directions on the drawing surface of FIG. 1. These terms representing the directions should not be considered as limitation to position and orientation of each component to be placed.

(1) Overview of HIFU Irradiation System

FIG. 1 shows a HIFU irradiation system 100 according to an embodiment of the present invention. In FIG. 1, the right direction on the drawing sheet is defined as an x axis positive direction. Further, a direction extending from the drawing sheet toward a viewer is defined as a y axis positive direction, and a downward direction on the drawing sheet is defined as a z axis direction. The HIFU irradiation system 100 includes a HIFU transducer unit 10, an ultrasound probe 12, a water bag 14, a probe driving device 16, a data acquiring device 18, a transducer controlling device 20, a display device 22, and a controller 24.

The HIFU transducer unit 10 includes a transducer housing 26 formed in a bowl shape with an opening facing downward, and a plurality of ultrasonic transducers 28 fixed to the transducer housing 26. The shape of the transducer housing 26 may be similar to the shape of a side surface of a cone. As used herein, the cone denotes a three-dimensional geometric shape formed by a set of straight lines extending from one point in a space toward the bottom. Alternatively, the transducer housing 26 may have an upwardly swollen shape like a dome. Each of the ultrasonic transducers 28 is fixed to the transducer housing 26 in such a manner that the intensity of an ultrasound wave emitted from each of the ultrasonic transducers 28 is enhanced at a treatment datum point P defined below the transducer housing 26.

The controller 24 may be a personal computer, a tablet computer, or the like. The controller 24 is connected to an operating device (not illustrated) used by a user to operate the HIFU irradiation system 100. The operating device may include a mouse, a touch panel integrated with the display device 22, a switch, a keyboard, and the like.

The transducer controlling device 20 operates, under the control of the controller 24, each of the ultrasonic transducers 28 to generate an ultrasound wave. In addition, the transducer controlling device 20 adjusts the intensity of the ultrasound wave generated by each of the ultrasonic transducers 28 under the control of the controller 24.

The ultrasound probe 12 is fixed to the transducer housing 26 so as to transmit and receive the ultrasound wave at a position located below the transducer housing 26 and above the treatment datum point P. In this embodiment, the ultrasound probe 12 penetrates a top portion of the transducer housing 26 along a vertical direction, with a transmission/reception part 30 pointing downward, the transmission/reception part 30 being configured to transmit/receive the ultrasound wave.

The water bag 14 is provided below the HIFU transducer unit 10 to match an acoustic impedance between each ultrasonic transducer 28 and a patient 34 with an acoustic impedance between the ultrasound probe 12 and the patient 34. The water bag 14 may be a bag filled with a material, such as water. The ultrasound probe 12 is inserted into the water bag 14 from a top portion thereof, so that the transmission/reception part 30 is located within the water bag 14.

The data acquiring device 18 may be implemented by an ultrasound diagnostic apparatus. The data acquiring device 18 performs, under the control of the controller 24, processing described below. That is, the data acquiring device 18 operates the ultrasound probe 12 to transmit an ultrasound wave and scan a beam (ultrasound beam) formed by the transmitted ultrasound wave. The ultrasound beam is scanned on an observation plane containing a center axis 36 of the transducer housing 26 vertically extending from the top of the transducer housing 26. The data acquiring device 18 operates the ultrasound probe 12 to receive a reflected ultrasound wave incoming from a direction along which the ultrasound beam is transmitted, and acquires a reception signal based on a reflected ultrasound wave received from each direction along which the ultrasound beam is transmitted. The data acquiring device 18 generates, based on the reception signal acquired in the observation plane, ultrasound data and outputs the generated ultrasound data to the controller 24. The ultrasound data may be, for example, data indicative of a B mode image (tomographic image) acquired with respect to the observation plane.

The probe driving device 16 rotates the ultrasound probe 12 about the center axis 36 under the control of the controller 24, to accordingly rotate the observation plane of the ultrasound probe 12 about the center axis 36.

When a medical treatment is performed, the water bag 14, the ultrasound probe 12, and the HIFU transducer unit 10 are positioned so as to allow a lower portion of the water bag 14 to come into full contact with the patient 34. Before a therapeutic ultrasound wave is applied from the HIFU transducer unit 10 to the patient 34, a positioning process is performed as described below.

The transducer controlling device 20 operates each of the ultrasonic transducers 28 installed in the HIFU transducer unit 10 to transmit an ultrasound wave having an intensity lower than that of an ultrasound wave used during the medical treatment. The probe driving device 16 sets a rotation angle position of the ultrasound probe 12 for allowing the ultrasound probe 12 to scan the ultrasound beam in the observation plane located at a predetermined rotation angle position. The data acquiring device 18 operates the ultrasound probe 12 to scan the ultrasound bean in the observation plane, to thereby acquire ultrasound data, and transmits the acquired ultrasound data to the controller 24. The controller 24 operates the display device 22 to display a B mode image represented by the ultrasound data and an image showing the treatment datum point P overlaid on the B mode image. The user working as a medical practitioner checks, with reference to the images displayed on the display device 22, a difference between a position of the treatment datum point P and a position (focal point) at which the ultrasound wave transmitted from the HIFU transducer unit 10 is enhanced.

When the difference between the position of the focal point and the treatment datum point P is out of a permissible range, the user changes positions or orientations of the water bag 14, the ultrasound probe 12, and the HIFU transducer unit 10. Alternatively, the user changes a state of contact between the water bag 14 and the patient 34. After ensuring that the position of the focal point is coincide with the position of the treatment datum point Por that the difference between the positions of the focal point and the treatment datum point P lies within the permissible range, the user performs an operation on the controller 24 to implement the medical treatment. The controller 24 controls the transducer controlling device 20 in accordance with the operation by the user. The transducer controlling device 20 operates, in response to the control of the controller 24, each of the ultrasonic transducers 28 to transmit the therapeutic ultrasound wave having an intensity necessary for the medical treatment. In this way, biological tissue located at the focal point is cauterized, so that the medical treatment is applied.

(2) Inspection of HIFU Transducer Unit

In the HIFU irradiation system 100, properties of the ultrasonic transducers 28 may be varied due to an impact exerted from the outside, changes by aging, or other factors. This may, in some cases, cause the focal point to deviate from an ideal position or decrease the intensity of the therapeutic ultrasound wave at the focal point. To avoid such a deviation or a decrease, the HIFU irradiation system 100 according to this embodiment performs a transducer inspection prior to commencing the medical treatment as described below.

In the transducer inspection, a phantom 38 simulating the patient 34 is used in place of the patient 34. Specifically, the water bag 14, the ultrasound probe 12, and the HIFU transducer unit 10 are positioned in such a manner that the water bag 14 is brought into intimate contact with the phantom 38. Further, among the plurality of ultrasonic transducers 28 arranged along a virtual bowl-shaped surface, only ultrasound transducers 28 arranged at a pair of segmented surfaces opposed to each other across the center axis 36 transmit the ultrasound waves, the pair of segmented surfaces being contained in a plurality of segmented surfaces obtained by segmenting the virtual bowl-shaped surface at a plurality of cutting planes containing the center axis 36.

Figure 2:
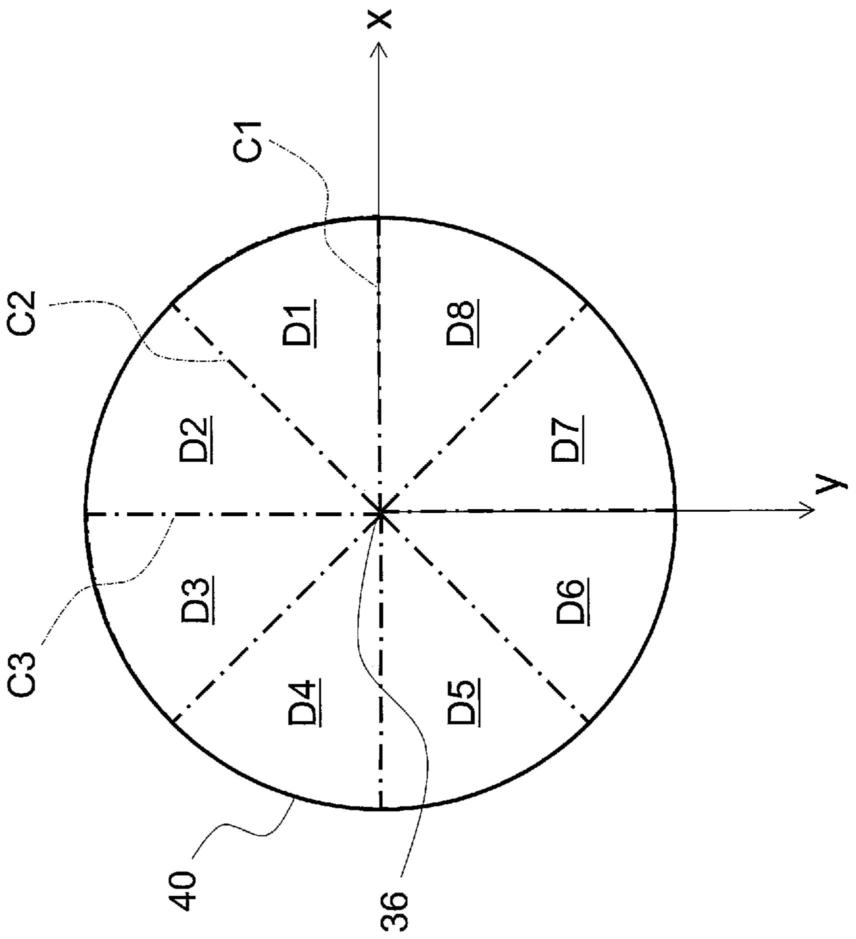
FIG. 2 is a diagram schematically showing a bowl-shaped surface viewed from above.

FIG. 2 schematically shows a bowl-shaped surface 40 viewed from above. In the example shown in FIG. 2, the bowl-shaped surface 40 is segmented at equal angular intervals of 45° by three cutting planes C1 to C3 containing the center axis 36 to form eight segmented surfaces D1 to D8. Each of angles formed between the cutting planes C1 and C2 and between the cutting planes C2 and C3 is 45°, and each of the segmented surfaces occupies a 45-degree angular range in the x-y plane. When an azimuth angle in the x axis positive direction is taken as 0° and a counterclockwise direction viewed from above is taken as the positive direction of the azimuth angle, a segmented surface Dj occupies a range from an azimuth angle greater than or equal to (45°×(j−1)) to an azimuth angle smaller than (45°×j), where j is an integer from 1 to 8.

The segmented surfaces D1 and D5 are opposed to each other across the center axis 36, and the segmented surfaces D2 and D6 are opposed to each other across the center axis 36. Further, the segmented surfaces D3 and D7 are opposed to each other across the center axis 36, and the segmented surfaces D4 and D8 are opposed to each other across the center axis 36.

The transducer controlling device 20 selects a pair of segmented surfaces Dk and D(k+4) from a plurality of pairs of segmented surfaces which are opposed to each other across the center axis 36, and causes ultrasonic transducers 28 positioned at the pair of segmented surfaces selected from the plurality of pairs of segmented surfaces to transmit the ultrasound wave having an intensity lower than that of the ultrasound wave used for the medical treatment. Here, k is any one of integers from 1 to 4. In addition, the probe driving device 16 sets the rotation angle position of the ultrasound probe 12 in such a manner that the rotation angle position of the observation plane is located in a range of azimuth angles occupied by a transmitting segmented surface. Here, the transmitting segmented surface denotes the pair of segmented surfaces Dk and D (k+4) on which the ultrasonic transducers 28 operated to transmit the ultrasound wave are placed.

For example, when k=1; i.e., when the transmitting segmented surface is composed of the segmented surface D1 and D5, the range of azimuth angles occupied by the transmitting segmented surface includes a range of azimuth angles greater than or equal to 0° and smaller than 45° and a range of azimuth angles greater than or equal to 180° and smaller than 225°. Therefore, the probe driving device 16 sets the rotation angle position of the ultrasound probe 12 so as to obtain the observation plane at a rotation angle position in the range of azimuth angles greater than or equal to 0° and smaller than 45° or in the range of azimuth angles greater than or equal to 180° and smaller than 225°. It should be noted that in terms of the observation plane being a plane, the range from 0° to less than 45° and the range from 180° to less than 225° are considered to be the same range.

When k=3; i.e., the transmitting segmented surface is composed of the segmented surfaces D3 and D7, the probe driving device 16 sets the rotation angle position of the ultrasound probe 12 so as to obtain the observation plane at an angle position in a range of azimuth angles greater than or equal to 90° and smaller than 135° and in a range of azimuth angles greater than or equal to 270° and smaller than 315°.

Alternatively, the probe driving device 16 may set the rotation angle position of the ultrasound probe 12 in such a manner that the rotation angle position of the observation plane is located at the center azimuth angle in the range of azimuth angles occupied by the transmitting segmented surface. For example, when the transmitting segmented surface is composed of the segmented surfaces D1 and D5 (when k=1), the probe driving device 16 may set the rotation angle position of the ultrasound probe 12 in such a manner that the rotation angle position of the observation plane is located at azimuth angles of 22.5° and 202.5°. Similarly, when the transmitting segmented surface is composed of the segmented surfaces D3 and D7 (when k=3), the probe driving device 16 may set the rotation angle position of the ultrasound probe 12 in such a manner that the rotation angle position of the observation plane is located at azimuth angles of 112.5° and 292.5°.

After the rotation angle position of the observation plane is set to the rotation angle position corresponding to the transmitting segmented surface, the data acquiring device 18 operates the ultrasound probe 12 to scan the ultrasound beam and acquires the reception signal based on the reflected ultrasound wave received from each direction in which the ultrasound beam is emitted. The data acquiring device 18 generates ultrasound data based on the reception signal acquired in the observation plane and outputs the generated ultrasound data to the controller 24.

The controller 24 measures an intensity Lk of the ultrasound wave at the treatment datum point P based on the ultrasound data acquired for the segmented surfaces Dk and D (k+4). In the following explanation, the intensity of the ultrasound wave (ultrasound intensity) at the treatment datum point P may be referred to as a datum point intensity.

The probe driving device 16, the data acquiring device 18, the transducer controlling device 20, and the controller 24 obtain datum point intensities Lk for all values of k in sequence. In the above-described example, the probe driving device 16, the data acquiring device 18, the transducer controlling device 20, and the controller 24 sequentially obtain the datum point intensity Lk for each value from k=1 to k=4. After the datum point intensity Lk is obtained for a previous pair of segmented surfaces (previous transmitting segmented surface), a process to obtain the datum point intensity Lk for a subsequent pair of segmented surfaces (subsequent transmitting segmented surface) may be initiated by the user, or may be automatically initiated under the control of the controller 24.

Figure 3A:
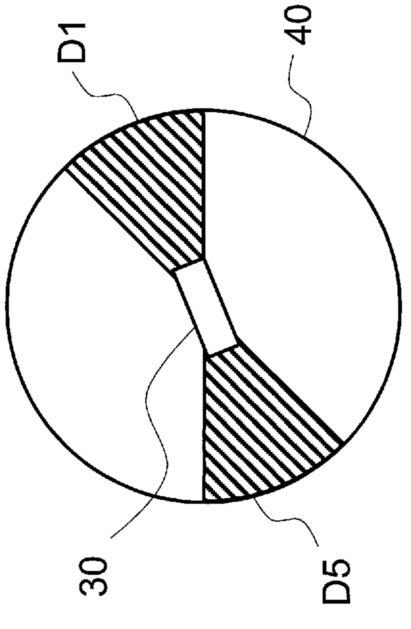
FIG. 3A is a diagram showing a pair of segmented surfaces serving as a transmission segmented surface.
Figure 3B:
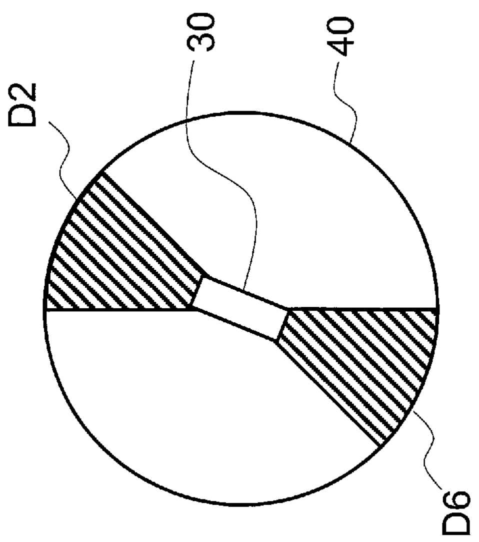
FIG. 3B is a diagram showing another pair of segmented surfaces serving as a transmission segmented surface.
Figure 3C:
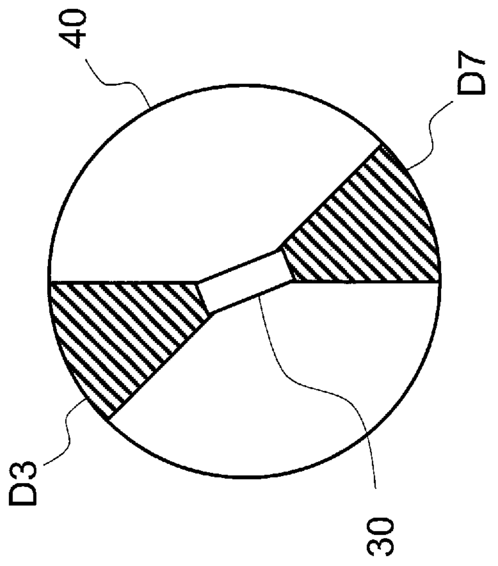
FIG. 3C is a diagram showing a further pair of segmented surfaces serving as a transmission segmented surface.
Figure 3D:
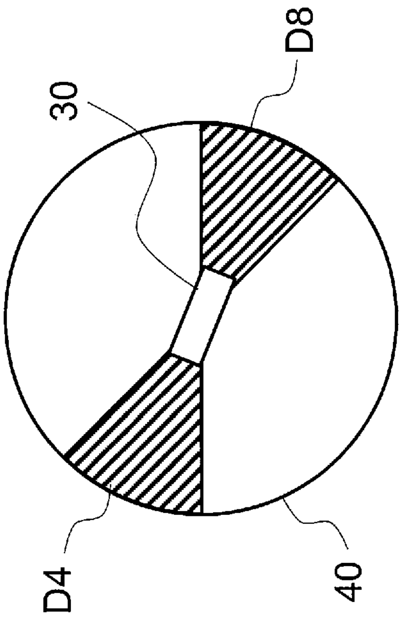
FIG. 3D is a diagram showing a still further pair of segmented surfaces serving as a transmission segmented surface.

In FIG. 3A, the pair of segmented surfaces D1 and D5 serving as the transmitting segmented surface when k=1 are indicated by hatching, and the transmission/reception part 30 of the ultrasound probe 12 is indicated by a rectangle at the center of the bowl-shaped surface 40. The longitudinal direction of the rectangle representing the transmission/reception part 30 indicates an azimuth in which the observation plane extends. In FIG. 3B, the pair of segmented surfaces D2 and D6 serving as the transmitting segmented surface when k=2 are indicated by hatching, and the transmission/reception part 30 of the ultrasound probe 12 is indicated at the center of the bowl-shaped surface 40. Using the same notational conventions, FIGS. 3C and 3D respectively show pairs of segmented surfaces serving as the transmitting segmented surfaces when k=3 and when k=4 and the transmission/reception part 30 of the ultrasound probe 12.

Based on the datum point intensity obtained for each of the plurality of pairs of segmented surfaces, the controller 24 determines a state of the ultrasonic transducer 28 associated with a corresponding one of the plurality of pairs of segmented surface. For example, the controller 24 calculates an average value of the datum point intensities Lk obtained for all values of k. When it is found in connection with a particular pair of segmented surfaces (transmitting segmented surface) that the absolute value of a difference calculated by subtracting the average value from a datum point intensity obtained for the particular pair exceeds a predetermined value, the controller 24 determines that ultrasonic transducers 28 positioned at the particular pair of segmented surfaces have abnormalities. Alternatively, when it is found that the absolute value of a difference calculated by subtracting a predetermined reference value from a datum point intensity obtained for the particular pair of segmented surfaces exceeds a predetermined value, the controller 24 may determine that ultrasonic transducers 28 positioned at the particular pair of segmented surfaces have abnormalities. The reference value may be a value previously defined through an experiment, a simulation, or the like.

When the controller 24 finds, in the plurality of pairs of segmented surfaces, a pair of segmented surfaces determined to have abnormal ultrasonic transducers 28, the controller 24 may display on the display device 22 information identifying the found pair of segmented surfaces.

(3) Display Process

Figure 4:
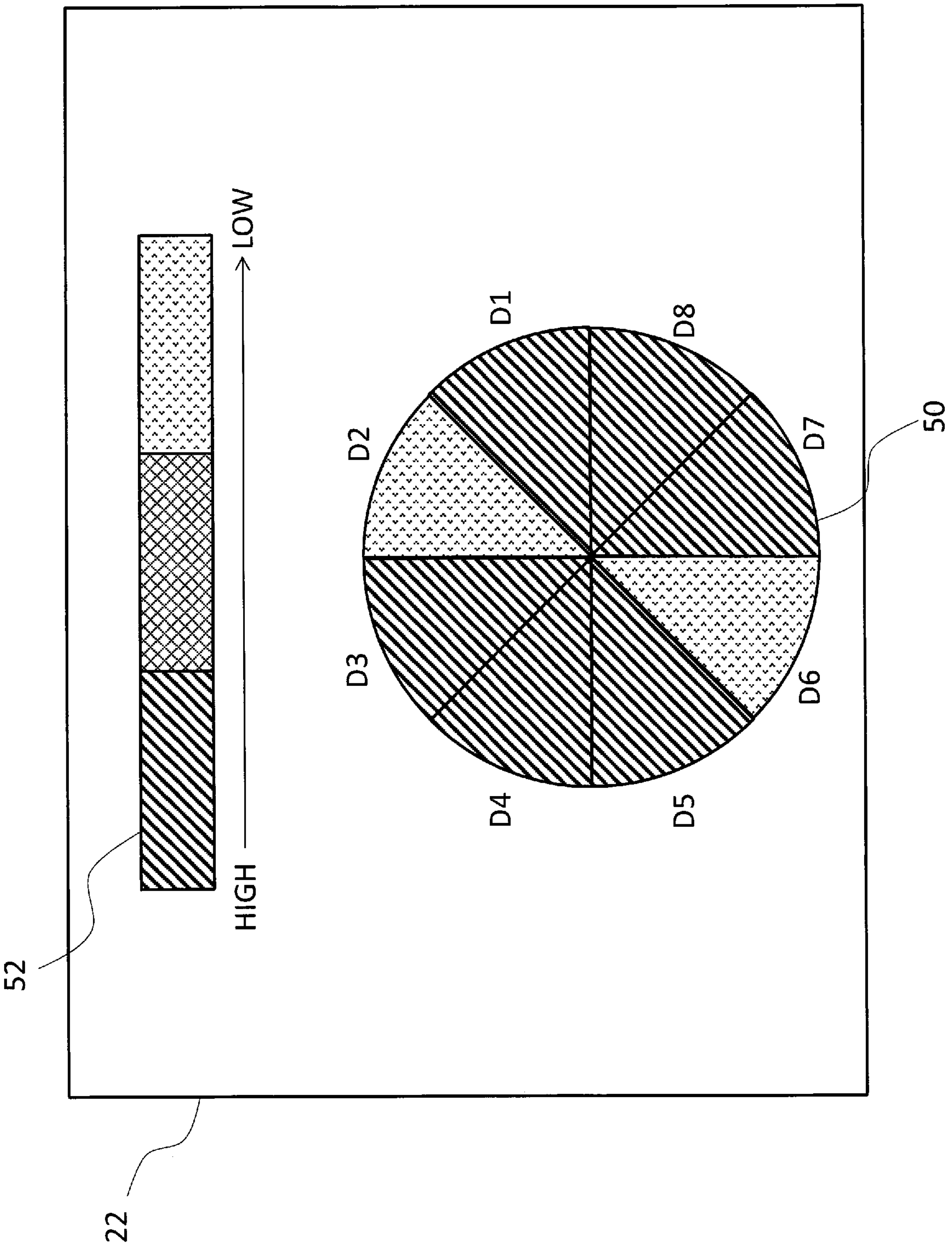
FIG. 4 is a diagram showing an example of an image displayed on a display device.

The controller 24 may display on the display device 22 information representing the datum point intensities respectively found for the plurality of pairs of segmented surfaces. The user may determine whether or not the ultrasonic transducer 28 has any abnormalities, with reference to the information shown on the display device 22. FIG. 4 shows an example of an image displayed on the display device 22 by the controller 24.

In the image, the segmented surfaces D1 to D8 are schematically represented by fan shapes obtained by segmenting a circular shape 50 into eight sectors at equal angular intervals. The fan shapes representing the segmented surfaces D1 to D8 are colored. An intensity criteria diagram 52 is shown in an upper region of the image. The intensity criteria diagram 52 shows the datum point intensities with ranges classified into three stages from greater values toward smaller values and indicates colors corresponding to the ranges. Specifically, the color given to a band-shaped region on the left end is associated with segmented surfaces having greater (higher) datum point intensities, and the color given to a band-shaped region on the right side is associated with segmented surfaces having smaller (lower) datum point intensities. The color given to a band-shaped region at the center is associated with segmented surfaces having middle datum point intensities.

With reference to the image shown on the display device 22, the user checks whether there is a pair of segmented surfaces having a datum point intensity smaller than those of the other segmented surfaces. When such a pair of segmented surfaces having the datum point intensity smaller than those of the other segmented surfaces is found, the user may determine that ultrasonic transducers 28 positioned at the found pair of segmented surfaces have abnormalities.

In the example shown in FIG. 4, the datum point intensity associated with the pair of segmented surfaces D2 and D6 is smaller than datum point intensities associated with the other segmented surfaces. For this reason, the user may determine that one or more ultrasonic transducers 28 positioned at the pair of segmented surfaces D2 and D6 have abnormalities.

Here, the example explained herein represents the datum point intensities in the three ranges classified from greater values toward smaller values in the intensity criteria diagram 52. The intensity criteria diagram 52 may show the datum point intensities in two ranges or four or more ranges classified from greater values toward smaller values. Alternatively, levels of the datum point intensities may be indicated with different patterns, such as mesh patterns, rather than indicating the levels of datum point intensities with colors.

The controller 24 may display on the display device 22, in addition to or in place of the fan shapes, numerical values of the datum point intensities respectively associated with the segmented surfaces. When it is found that the absolute value of a difference calculated by subtracting the predetermined reference value from a datum point intensity obtained for a particular pair of segmented surfaces exceeds the predetermined value, the user may determine that ultrasonic transducers 28 positioned at the particular pair of segmented surfaces have abnormalities.

(4) Inspection of Coupling State

The embodiment in which it is determined whether or not the ultrasonic transducer 28 has an abnormality has been described above as an inspection of the state of the ultrasonic transducer 28. In the HIFU irradiation system 100, it may be determined whether or not a state of ultrasonic coupling (coupling state) between the ultrasonic transducer 28 and the patient 34 is favorable. In this case, as shown in FIG. 1, the water bag 14, the ultrasound probe 12, and the HIFU transducer unit 10 are positioned so as to bring the lower part of the water bag 14 into intimate contact with the patient 34.

The probe driving device 16, the data acquiring device 18, the transducer controlling device 20, and the controller 24 sequentially find the datum point intensities Lk for all values of k by performing operation as in the case of determining the presence or absence of an abnormality in the ultrasonic transducer 28. After the datum point intensity Lk is obtained for the previous pair of segmented surfaces, the process to obtain the datum point intensity Lk for a subsequent pair of segmented surfaces may be initiated by the user, or may be automatically initiated under the control of the controller 24.

Based on the datum point intensities obtained for each of the plurality of pairs of segmented surfaces, the controller 24 determines a state of the ultrasonic transducer 28 associated with a corresponding one of the plurality of pairs of segmented surfaces. For example, the controller 24 calculates an average value of the datum point intensities Lk obtained for all values of k. When it is found in connection with a particular pair of segmented surfaces that the absolute value of a difference calculated by subtracting the average value from a datum point intensity obtained for the particular pair of segmented surfaces exceeds a predetermined value, the controller 24 determines that coupling states of ultrasonic transducers 28 positioned at the particular pair of segmented surfaces are unfavorable. Alternatively, when the absolute value of a difference calculated by subtracting a predetermined reference value from a datum point intensity obtained for a particular pair of segmented surfaces exceeds a predetermined value, the controller 24 may determine that coupling states of ultrasonic transducers 28 positioned at the particular pair of segmented surfaces are unfavorable.

When the controller 24 finds, in the plurality of pairs of segmented surfaces, a pair of segmented surfaces determined to have ultrasonic transducers 28 being in unfavorable coupling states, the controller 24 may display on the display device 22 information identifying the found pair of segmented surfaces. In addition, the controller 24 may store coupling information identifying the found pair of segmented surfaces with respect for which the unfavorable coupling states are determined. During a medical treatment, the controller 24 may control, with reference to the coupling information, the transducer controlling device 20 to reduce the intensity of a therapeutic ultrasound wave from the ultrasonic transducers 28 on the segmented surfaces with respect for which the unfavorable coupling states are determined.

Figure 5:
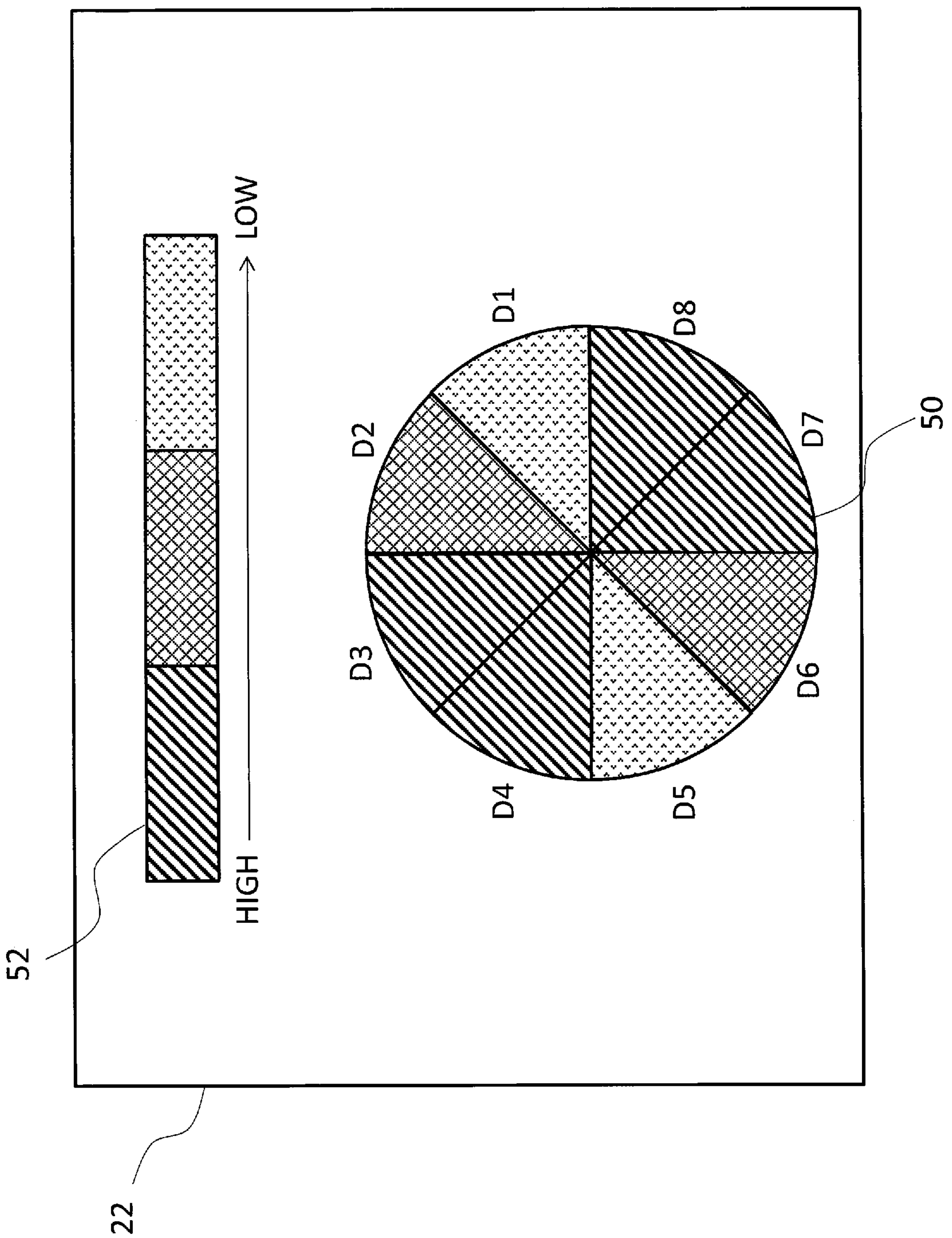
FIG. 5 is a diagram showing another example of the image displayed on the display device.

Also, in the inspection of the coupling state, the controller 24 may display, on the display device 22, information representing the datum point intensities respectively obtained for the plurality of pairs of segmented surfaces. The user may determine, with reference to the information displayed on the display device 22, whether or not the coupling state of the ultrasonic transducer 28 is favorable. FIG. 5 shows an example of an image displayed on the display device 22 by the controller 24.

In the example shown in FIG. 5, datum point intensities corresponding to the segmented surfaces D1 and D5 and corresponding to the segmented surfaces D2 and D6 are relatively small. Because the segmented surfaces D1 and D5 have the smallest datum point intensity, the user may determine that the ultrasonic transducers 28 on the segmented surfaces D1 and D5 are in an unfavorable coupling state.

The user may operate the controller 24 to store the coupling information identifying the pair of segmented surfaces with respect for which the unfavorable coupling states are determined. During the medical treatment, the controller 24 controls, with reference to the coupling information, the transducer controlling device 20 to reduce the intensity of a therapeutic ultrasound wave from the ultrasonic transducers 28 on the segmented surfaces with respect for which the unfavorable coupling states are determined.

Also, in the inspection of the coupling state, the controller 24 may display on the display device 22, in addition to or in place of the fan shapes, numerical values of the datum point intensities respectively associated with the pairs of segmented surfaces. When it is found that the absolute value of a difference, which is calculated by subtracting the predetermined reference value from a datum point intensity obtained for a particular pair of segmented surfaces, exceeds the predetermined value, the user may determine that coupling states of ultrasonic transducers 28 positioned at the particular pair of segmented surfaces are unfavorable.

The embodiment in which the state of the ultrasonic transducer 28 is inspected based on the eight segmented surfaces obtained by segmenting the bowl-shaped surface 40 at the intervals of 45° has been described above. Other than the angular intervals of 45°, the bowl-shaped surface 40 may be segmented at an angular interval of 360° divided by 4 or by a greater even number.

(5) Method Employed in HIFU Irradiation System and Effect Thereof

In the HIFU irradiation system 100, the ultrasonic transducer inspection apparatus is composed of the probe driving device 16, the data acquiring device 18, the transducer controlling device 20, and the controller 24, and an inspection is performed on the plurality of ultrasonic transducers 28 arranged along the bowl-shaped surface 40. In this inspection, a selection and observation process is performed on each of the plurality of pairs of segmented surfaces, and the selection and observation process includes steps (i) to (iv) described below.

(i) A step of selecting a pair of segmented surfaces from a plurality of pairs of segmented surfaces obtained by segmenting the bowl-shaped surface 40 at a plurality of cutting planes including the center axis 36 of the bowl-shaped surface 40; i.e., a plurality of segmented surfaces opposed to each other across the center axis 36.

(ii) A step of operating the ultrasonic transducers 28 positioned at the pair of segmented surfaces selected from the plurality of pairs of segmented surfaces to transmit ultrasound waves.

(iii) A step of setting the ultrasound probe 12 in a state of scanning ultrasound beams in an observation plane passing through the pair of segmented surfaces selected from the plurality of pairs of segmented surfaces.

(iv) A step of acquiring ultrasound data for the observation plane where the ultrasound beams are scanned.

The ultrasound data is acquired for each of the plurality of pairs of segmented surfaces by performing the selection and observation process on the each of the plurality of pairs of segmented surfaces, and states of the ultrasonic transducers 28 positioned at a corresponding one of the plurality of pairs of segmented surfaces are determined. Determining the states of the ultrasonic transducers 28 includes determining whether or not the ultrasonic transducer 28 has an abnormality, and determining whether or not the coupling state of the ultrasonic transducer 28 is favorable.

According to the above-described method, the states of the ultrasonic transducers 28 can be identified without the necessity of newly installing a measuring instrument. In addition, processes, such as a process of removing the ultrasonic transducers 28 from the HIFU irradiation system 100, can be eliminated. Accordingly, the states of the ultrasonic transducers 28 can be easily identified.

REFERENCE SIGNS LIST

10 HIFU transducer unit, 12 ultrasound probe, 14 water bag, 16, probe driving device, 18 data acquiring device, 20 transducer controlling device, 22 display device, 24 controller, 26 transducer housing, 28 ultrasonic transducer, 30 transmission/reception part, 34 patient, 36 center axis, 38 phantom, 40 bowl-shaped surface, 100 HIFU irradiation system.

The invention claimed is:

1. An ultrasonic transducer inspection apparatus, comprising:

a transducer controlling device configured to control a plurality of ultrasonic transducers arranged along a bowl-shaped surface;

a probe driving device configured to rotate an ultrasound probe positioned at a center axis of the bowl-shaped surface around the center axis;

a data acquiring device configured to acquire ultrasound data using the ultrasound probe; and a controller configured to control the transducer controlling device, the probe driving device, and the data acquiring device, wherein prior to a medical treatment using the ultrasonic transducers, the controller controls the transducer controlling device to transmit an ultrasound wave from the ultrasonic transducer positioned at a pair of segmented surfaces opposed to each other across the center axis, the pair of segmented surfaces being contained in a plurality of segmented surfaces obtained by segmenting the bowl-shaped surface at a plurality of cutting planes containing the center axis; and performs a selection and observation process which comprises selecting the pair of segmented surfaces from a plurality of pairs of segmented surfaces opposed to each other across the center axis, controlling the transducer controlling device to transmit an ultrasound wave having an intensity lower than that used for the medical treatment from the ultrasound transducer positioned at the pair of segmented surfaces selected from the plurality of pairs of segmented surfaces, controlling the probe driving device to set the ultrasound probe in a state of scanning an ultrasound beam in an observation plane passing through the pair of segmented surfaces selected from the plurality of pairs of segmented surfaces, and controlling the data acquiring device to acquire the ultrasound data on the observation plane where the ultrasound beam is scanned, the selection and observation process being performed on each of the plurality of pairs of segmented surfaces, and wherein prior to the medical treatment using the ultrasound transducers, the controller performs, on each of the plurality of pairs of segmented surfaces, a process to find, based on the ultrasound data, an ultrasound intensity at a treatment datum point defined for the plurality of ultrasonic transducers, and displays on a display device information associated with the ultrasound intensity found for the each of the plurality of pairs of segmented surfaces.

2. The ultrasonic transducer inspection apparatus according to claim 1, wherein the controller is configured to determine, based on the ultrasound intensity found for the each of the plurality of pairs of segmented surfaces, states of the ultrasonic transducers which are respectively associated with the plurality of pairs of segmented surfaces.

3. The ultrasonic transducer inspection apparatus according to claim 1, wherein the controller is configured to determine, based on a comparison between a reference value and the ultrasound intensity found for the each of the plurality of pairs of segmented surfaces, states of the ultrasonic transducers which are respectively associated with the plurality of pairs of segmented surfaces.

4. An ultrasonic transducer inspection apparatus, comprising:

a transducer controlling device configured to control a plurality of ultrasonic transducers arranged along a bowl-shaped surface;

a probe driving device configured to rotate an ultrasound probe positioned at a center axis of the bowl-shaped surface around the center axis;

a data acquiring device configured to acquire ultrasound data using the ultrasound probe; and a controller configured to control the transducer controlling device, the probe driving device, and the data acquiring device, wherein the controller controls the transducer controlling device to transmit an ultrasound wave from the ultrasonic transducer positioned at a pair of segmented surfaces opposed to each other across the center axis, the pair of segmented surfaces being contained in a plurality of segmented surfaces obtained by segmenting the bowl-shaped surface at a plurality of cutting planes containing the center axis; and performs a selection and observation process which comprises selecting the pair of segmented surfaces from a plurality of pairs of segmented surfaces opposed to each other across the center axis, controlling the transducer controlling device to transmit an ultrasound wave from the ultrasound transducer positioned at the pair of segmented surfaces selected from the plurality of pairs of segmented surfaces, controlling the probe driving device to set the ultrasound probe in a state of scanning an ultrasound beam in an observation plane passing through the pair of segmented surfaces selected from the plurality of pairs of segmented surfaces, and controlling the data acquiring device to acquire the ultrasound data on the observation plane where the ultrasound beam is scanned, the selection and observation process being performed on each of the plurality of pairs of segmented surfaces, wherein the controller performs, on each of the plurality of pairs of segmented surfaces, a process to find, based on the ultrasound data, an ultrasound intensity at a treatment datum point defined for the plurality of ultrasonic transducers; and determines, based on the ultrasound intensity found for the each of the plurality of pairs of segmented surfaces, states of the ultrasonic transducers which are respectively associated with the plurality of pairs of segmented surfaces.

5. The ultrasonic transducer inspection apparatus according to claim 4, wherein the controller displays on a display device information associated with the ultrasound intensity found for each of the plurality of pairs of segmented surfaces.

6. An inspection method for inspecting a plurality of ultrasonic transducers arranged along a bowl-shaped surface, the inspection method comprising:

selecting a pair of segmented surfaces from a plurality of pairs of segmented surfaces obtained by segmenting the bowl-shaped surface at a plurality of cutting planes containing a center axis of the bowl-shaped surface, the plurality of pairs of segmented surfaces being opposed to each other across the center axis;

transmitting an ultrasound wave from the ultrasonic transducers positioned at the selected pair of segmented surfaces;

setting an ultrasound probe in a state of scanning an ultrasound beam in an observation plane passing through the selected pair of segmented surfaces;

performing, on each of the plurality of pairs of segmented surfaces, a selection and observation process to acquire ultrasound data on the observation plane where the ultrasound beam is scanned; and determining, based on the ultrasound data acquired for the each of the plurality of pairs of segmented surfaces, states of the ultrasonic transducers which are respectively associated with the plurality of pairs of segmented surfaces.

7. The inspection method according to claim 6, wherein determining states of the ultrasonic transducers which are respectively associated with the plurality of pairs of segmented surfaces comprises performing, on each of the plurality of pairs of segmented surfaces, a process to find, based on the ultrasound data, an ultrasound intensity at a treatment datum point defined for the plurality of ultrasonic transducers; and determining, based on the ultrasound intensity found for the each of the plurality of pairs of segmented surfaces, the states of the ultrasonic transducers which are respectively associated with the plurality of pairs of segmented surfaces.

8. An ultrasonic transducer inspection apparatus, comprising:

a transducer controlling device configured to control a plurality of ultrasonic transducers arranged along a bowl-shaped surface;

a probe driving device configured to rotate an ultrasound probe positioned at a center axis of the bowl-shaped surface around the center axis;

a data acquiring device configured to acquire ultrasound data using the ultrasound probe; and a controller configured to control the transducer controlling device, the probe driving device, and the data acquiring device, wherein the controller controls the transducer controlling device to transmit an ultrasound wave from the ultrasonic transducer positioned at a pair of segmented surfaces opposed to each other across the center axis, the pair of segmented surfaces being contained in a plurality of segmented surfaces obtained by segmenting the bowl-shaped surface at a plurality of cutting planes containing the center axis; and performs a selection and observation process which comprises selecting the pair of segmented surfaces from a plurality of pairs of segmented surfaces opposed to each other across the center axis, controlling the transducer controlling device to transmit an ultrasound wave from the ultrasound transducer positioned at the pair of segmented surfaces selected from the plurality of pairs of segmented surfaces, controlling the probe driving device to set the ultrasound probe in a state of scanning an ultrasound beam in an observation plane passing through the pair of segmented surfaces selected from the plurality of pairs of segmented surfaces, and controlling the data acquiring device to acquire the ultrasound data on the observation plane where the ultrasound beam is scanned, the selection and observation process being performed on each of the plurality of pairs of segmented surfaces, wherein the controller performs, on each of the plurality of pairs of segmented surfaces, a process to find, based on the ultrasound data, an ultrasound intensity at a treatment datum point defined for the plurality of ultrasonic transducers; and determines, based on a comparison between a reference value and the ultrasound intensity found for the each of the plurality of pairs of segmented surfaces, states of the ultrasonic transducers which are respectively associated with the plurality of pairs of segmented surfaces.

9. The ultrasonic transducer inspection apparatus according to claim 8, wherein the controller displays on a display device information associated with the ultrasound intensity found for each of the plurality of pairs of segmented surfaces.

* * * * *